(12) United States Patent
Döll

(10) Patent No.: US 10,674,781 B2
(45) Date of Patent: Jun. 9, 2020

(54) DEVICE FOR AVOIDING EXCESSIVE BURDENS ON THE HUMAN FOOT WHILE WALKING AND OPERATING METHOD THEREFOR

(71) Applicant: Walter Döll, Kehrsatz (CH)

(72) Inventor: Walter Döll, Kehrsatz (CH)

( * ) Notice: Subject to any disclaimer, the term of this patent is extended or adjusted under 35 U.S.C. 154(b) by 285 days.

(21) Appl. No.: 15/865,769

(22) Filed: Jan. 9, 2018

(65) Prior Publication Data

US 2018/0199656 A1 Jul. 19, 2018

(30) Foreign Application Priority Data

Jan. 13, 2017 (DE) .................. 10 2017 100 636

(51) Int. Cl.
*A43B 3/00* (2006.01)
*A61B 5/103* (2006.01)
(Continued)

(52) U.S. Cl.
CPC ............. *A43B 3/0005* (2013.01); *A43B 7/00* (2013.01); *A43B 13/38* (2013.01); *A43B 17/00* (2013.01); *A43B 23/00* (2013.01); *A61B 5/1036* (2013.01); *A61B 5/1038* (2013.01); *A61B 5/486* (2013.01); *A61B 5/6807* (2013.01); *A61B 5/7455* (2013.01); *G01L 1/205* (2013.01); *G09B 5/06* (2013.01); *G09B 19/003* (2013.01); *A61B 5/002* (2013.01); *A61B 2560/0214* (2013.01)

(58) Field of Classification Search
None
See application file for complete search history.

(56) References Cited

U.S. PATENT DOCUMENTS 4,745,930 A 5/1988 Confer
5,033,291 A 7/1991 Podoloff et al.
(Continued)

FOREIGN PATENT DOCUMENTS

CN 205080396 3/2016
DE 92 02 462.9 6/1992
(Continued)

OTHER PUBLICATIONS

Search Report for corresponding European Application No. 18151004 dated Jun. 6, 2018.

*Primary Examiner* — Jason T Yen
(74) *Attorney, Agent, or Firm* — Renner, Otto, Boisselle & Sklar, LLP

(57) ABSTRACT

A device for avoiding excessive loads on the human foot when walking comprises a shoe insole having at least one force sensor for generating a measurement signal indicating loads and/or partial loads on the foot; an analyzing unit electrically connected to the at least one force sensor for analyzing the measurement signal of the at least one force sensor; an electric power source to provide electric power to the analyzing unit; and a feedback control signal generator which generates a feedback control signal on the basis of the analysis of the analyzing unit for monitoring loads and/or partial loads on the foot, e.g., by means of an actuator, wherein the sensitive components are disposed in a housing to protect them, in particular from water and/or pressure loads. Furthermore, a method for operating the device is provided.

13 Claims, 6 Drawing Sheets

(51) Int. Cl.
*A61B 5/00* (2006.01)
*A43B 17/00* (2006.01)
*A43B 7/00* (2006.01)
*A43B 13/38* (2006.01)
*A43B 23/00* (2006.01)
*G01L 1/20* (2006.01)
*G09B 5/06* (2006.01)
*G09B 19/00* (2006.01)

(56) References Cited

U.S. PATENT DOCUMENTS

| | | | |
|---|---|---|---|
| 5,408,873 | A | 4/1995 | Schmidt et al. |
| 6,876,947 | B1 | 4/2005 | Darley et al. |
| 6,978,684 | B2 | 12/2005 | Nurse |
| 2004/0173220 | A1 | 9/2004 | Harry et al. |
| 2005/0097970 | A1* | 5/2005 | Nurse ............... A61H 3/00 73/862.041 |
| 2005/0261609 | A1 | 11/2005 | Collings et al. |
| 2008/0216593 | A1 | 9/2008 | Jacobsen et al. |
| 2014/0094873 | A1* | 4/2014 | Emborg ............ A43B 3/0005 607/49 |
| 2014/0260677 | A1* | 9/2014 | Dojan ............... A43B 13/12 73/862.045 |
| 2016/0143562 | A1* | 5/2016 | Ashby ............ A61B 5/1038 600/595 |
| 2016/0158622 | A1 | 6/2016 | Yamazaki |
| 2016/0375346 | A1* | 12/2016 | Czaja ............ A63C 11/003 434/253 |
| 2018/0038461 | A1* | 2/2018 | Salerno ............ B25J 9/12 |

FOREIGN PATENT DOCUMENTS

| | | |
|---|---|---|
| DE | 20 2007 016 709 | 5/2009 |
| DE | 10 2009 033 814 | 1/2011 |

* cited by examiner

DEVICE FOR AVOIDING EXCESSIVE BURDENS ON THE HUMAN FOOT WHILE WALKING AND OPERATING METHOD THEREFOR

FIELD OF INVENTION

The present invention generally relates to the avoidance of excessive loads on the human foot when walking, in particular in the field of rehabilitation or convalescence after surgery or in the field of orthopedics or physiotherapy, and relates in particular to providing a feedback signal by measuring loads and/or partial loads on a foot, analyzing the measurement and output of a feedback signal, and to an operating method thereof.

BACKGROUND OF INVENTION

As a result of the higher age due to medical progress and/or increased direct loads, such as from sport or work, the various joint parts of the human body are nowadays subjected to ever-increasing stress on average. In particular, the frequently used joint parts of the walking apparatus of the human body, such as the hips and knees, are to be mentioned here. In many cases, the respective joint is damaged to such an extent that a corresponding operation becomes indispensable. As a result, the number of hip and knee surgeries has risen dramatically over the last few decades and these surgeries have become a standard procedure in medical practice where a natural joint ball is replaced by prosthesis.

After such a surgery, the patient usually receives comprehensive physiotherapeutic instruction at first, but is largely on his own after leaving the clinic. In particular, incorrect, i.e. excessively high, loads caused by the patient may cause damage to the prosthesis or the surrounding tissue. To prevent this, various systems have been developed to monitor the load on the foot of a patient.

US 2016 158 622 A1 discloses a conventional walking training system comprising a treadmill and two frames that support the patient, wherein sensors measure the weight distribution while running. This system is a convention system used in physiotherapy. For private use, however, it is too expensive (because e.g. a treadmill is used), too bulky and too impractical (especially for everyday use).

U.S. Pat. No. 4,745,930 discloses a device integrated on a relatively narrow shoe sole, comprising sensor units provided in designated chambers and comprising pairs of electrical contacts which are alternately finger-shaped and can be pressed together by pressure to create an electrical contact. Unfortunately, however, this device is normally connected to a support frame via a cable for transmitting signals to it and also includes a sensitive sensor system that is integrated into the sole of the shoe and offers no readout options. This makes practical everyday use almost impossible.

US 2005 026 160 2005 026 1609 A1 discloses a device of a simple configuration integrated in a relatively wide shoe sole, comprising a state sensor that measures the physical state of the foot and an RF transmitter that sends a signal to an external display unit according to the measurement. The afore-mentioned status sensors are installed in special installation niches. Although this device is integrated into the sole of the shoe, the considerable width of the shoe's sole makes it uncomfortable. In addition, the measurement signals are transmitted by an RF transmitter, which requires an external receiver unit (e.g. a display wristband or a Smartphone) and an uninterrupted transmission path between the RF transmitter and the receiver unit.

U.S. Pat. No. 5,033,291 discloses a flexible sensor capable of measuring foot pressure distributions upon contact of the foot, said sensor comprising a plurality of flexible electrodes divided into two non-parallel sets for measuring these pressure distributions. In particular, the sensor is preferably designed in the shape of a foot. A similar flexible sensor system is also disclosed in U.S. Pat. No. 5,408,873, wherein several force sensor units may be positioned at the essential measuring points according to this invention. However, these sensors are relatively complex and expensive in their implementation as disclosed. Furthermore, the afore-mentioned disclosures do not provide for a feedback system.

In addition to the above-mentioned devices and systems from the medical sector, there exist also countless other systems that are used in the sports sector, most of which are only used for the direct measurement of training parameters, such as the contact time of the feet and the step frequency. Such a system is disclosed, for example, in U.S. Pat. No. 6,876,947 B1, which comprises a unit attached to the shoe that transmits measurement signals, such as the contact time of the foot, to a display unit (e.g. a Smartphone or smart watch) using RF transmission. Also this disclosure gives rise to the aforementioned problems that may arise during RF transmission and the problem of a missing (direct) feedback.

DESCRIPTION OF INVENTION

It is an object of the present invention to provide a low-cost device for everyday use that can measure and analyze the loads or partial loads on a foot in order to provide the user with direct feedback in a simple manner, in order to avoid excessive loads on the human foot when walking.

According to the present invention there is provided a device to avoid excessive loads on a human foot when walking. The device comprises a shoe insole, at least one force sensor, an analyzing unit, an electric power source, a feedback control signal generator and a feedback output unit. The at least one force sensor is arranged on or in the shoe insole to generate a measurement signal indicating loads and/or partial loads on the foot. The analyzing unit is electrically connected to the at least one force sensor for analyzing the measurement signal from the at least one force sensor. The electric power source provides electric power to the analyzing unit. On the basis of the analysis of the analyzing unit, the feedback control signal generator generates a feedback control signal, which controls the feedback output unit in order to output a feedback signal in the region of the foot. In this manner the device can generate a so-called bio-feedback in the region of the foot on the basis of measured loads and/or partial loads on the foot, i.e. loads and/or partial loads acting on the foot.

According to the present invention, the shoe insole should be kept as flat as possible in order to be able to replace a regular shoe insole in different shoes. The individual components, such as the force sensors or the conductive tracks for the electrical connection of the components, may either be fixed to the shoe insole in a non-detachable manner (e.g. by gluing, laminating, pouring, foaming etc.) or they may be attached to it (e.g. by means of adhesive bonding, lamination, pouring, foaming etc.), so that both embodiments are conceivable according to the present invention, in which the device is reused several times, e.g. as an installation in running shoes, or in which the device is used only a few times, e.g. in hospital operation. In particular, the shoe insole or foot orthosis may be disposed in conventional shoes as well as in medical devices similar to shoes.

The force sensors used may be implemented according to different embodiments. On the one hand, the force sensors are designed to be as flat as possible and, on the other hand, they are designed to be flexible and stretchable in order to adapt to the respective sole of the foot. In particular, force sensors based on foil-based sensors are suitable for this purpose to measure loads and/or partial loads on the human foot when walking. In this case, a foil sensor is deformed by applying pressure to a certain portion of the foot. Other force sensors, in particular capacitive force sensors, which are filled with a deformable dielectric and change their capacity when a force is applied from above, are also applicable in the sense of the invention.

According to the present invention, the electrical conductive paths or tracks may be available in different versions. In particular, these may be glued in cable-like structures to the shoe insole or integrated into it. However, it is also possible to apply the conductive tracks directly to the shoe sole by means of an 'electric circuit printing' process.

According to the present invention, the electric power source is preferably a commercially available button cell battery (as a primary element), although rechargeable cells are also possible. In particular, button cells with primary elements are of particular interest for embodiments of the present invention that are used temporarily, e.g. in the post-operative rehabilitation, whereas rechargeable batteries or replaceable batteries also play a role for embodiments that can be used permanently. In addition, additional miniature generators are also possible to recharge the electric power source (e.g. for 'energy harvesting') or combinations of the aforementioned examples.

As mentioned above, the feedback control signal generator generates a feedback control signal, wherein this feedback control signal is used to control different display devices. In particular, the controlling of actuators should be mentioned here, although additional display devices (e.g. optical or acoustic display devices) may also be provided. It is to be noted here that the feedback control signal generator may be embodied as a single unit or integrated in the analyzing unit. The second variant is preferred in particular for more powerful analyzing units, such as MCUs or even CPUs.

According to a further embodiment, the actuator is configured for generating, as a tactile feedback, vibrations on the housing or in the immediate vicinity of the housing. These act on in the region of the longitudinal arch of the foot and thus in a particularly sensitive area of a human foot, so that vibrations even with relatively low intensity, which can easily be generated in an power-saving manner, may be sufficient to provide a feedback about the walking behavior to the human being. This feedback should be generated in such a way that, when walking in an acceptable zone where the loads and/or partial loads on the human foot are within an acceptable range, no feedback is output, whereas in a zone where the loads and/or partial loads on the human foot are no longer within an acceptable range, for example because the foot is placed too far to the side or tilted, a tactile feedback is output which directly warns the patient and thus requests the patient to return to an acceptable walking zone. Here, the feedback may be output as a continuous or intermittent tactile feedback signal.

In a particularly preferred embodiment, the device further comprises a housing integrated into the shoe insole and comprising an electrical circuit board. Conveniently, the housing is sealed to a sufficient extent to reliably prevent moisture or even wetness from penetrating into the interior of the housing. This can easily be achieved by means of a sealing or by an appropriate shape of housing shells.

The housing may comprises/accommodate the analyzing unit, the electric power source and the feedback control signal generator and the feedback output unit in order to protect them. In particular, the protection against water, e.g. in the form of sweat or rainwater penetrating into the shoe, and the protection against high pressure loads, which can arise e.g. by putting on the foot when waling, should be mentioned here. The housing is preferably provided in the region of the foot longitudinal arch, because at this position there is sufficient space for fixing and additional protection, since the main pressure points of the foot are normally located in the region of the ball and/or heel and not in the region of the foot longitudinal arch. Furthermore, this region can also be stimulated easily and is therefore easily accessible for tactile signals. In addition, of course also embodiments may be considered in which a reinforced casing is arranged also in the region of the heel or ball. Furthermore, also a non-sealed housing is possible, wherein the housing may be opened, for example by loosening a clip or screw connection. This embodiment is conceived particularly in the clinical field, but especially in physiotherapy.

In addition to this central housing, however, several partial housings are also possible to protect individual sensitive components.

In a preferred embodiment, the device further comprises an I/O interface (input/output interface). By means of this I/O interface, the analyzing unit and other potential components can be programmed, wherein on the one hand it is possible to read in a certain "embedded firmware", or on the other hand it is possible to simply set certain adjustment parameters of the device, such as the sensitivity of the force sensors or a strength of the feedback. Further, it is also possible to read out the analyzing unit, e.g. for analyzing data on a computer or smartphone. The I/O interface may be embodied as a wired interface with detachable connector, e.g. as a USB connection, or preferably may be embodied as a wireless interface. For a wireless interface, a "Near Field Communication" NFC interface is particularly suitable, in which a transmission coil is arranged inside the sealed housing of the device and can be read out easily by an appropriate device, such as a smartphone. The NFC interface works alternately according to the principle of electromagnetic induction. For this purpose, an induction coil as large as possible is installed inside the shoe insole or inside the sealed housing. In a second function, the induction coil is also used for contactless charging of the electric power source if this should be rechargeable. This requires a special charging device that charges the electric power source overnight according to the principle of electromagnetic induction. This charging device may be designed, for example, as a floor mat with embedded induction coils for generating magnetic fields.

In a preferred form, the device further comprises a memory element. Analysis data from the analyzing unit can be stored on this memory element for later analysis, for example. Programs may also be stored on this unit. The memory element may either be permanently mounted (embedded chip) or removable (e.g. a flash card).

In a particularly preferred embodiment of the present invention, the device comprises at least one actuator as a feedback output unit, which receives the feedback control signal of the feedback control signal generator and generates a tactile feedback in the region of the shoe insole (foot orthosis). The strength of the tactile feedback may be adjusted to provide the user with an appropriate feedback. Various variants are available for the actuator design, whereby the actuators may be arranged both as rotating micro motors with eccentric members (analogous to the function of a vibration alarm in a mobile phone) and as vibrators with exclusively translational direction of movement. Alternatively, the actuator may also be configured in the same manner as a loudspeaker, wherein an excitation coil is firmly connected to the upper part of the sealed housing, while a permanent magnet is connected to the lower part of the sealed housing together with a soft magnetic guiding material for guiding the magnetic flow. When a varying current flows through the excitation coil, the excitation coil and the permanent magnet exert a force on each other which is transmitted to the foot longitudinal arch.

According to an embodiment of the present invention, the device comprises a plurality of force sensors and actuators distributed in the shoe insole. In this embodiment, the actuators are arranged close to a respective force sensor in order to generate tactile feedback at several positions of the shoe insole, so that the feedback output can be generated on the basis of the partial loads of the foot at these several positions of the shoe insole. This embodiment plays a role especially in the field of sports medicine and for training purposes, as it enables the user to break the habit of wrong running or of wrong load patterns in a simple manner in order to avoid a wide variety of damages, such as Achilles tendon distortions, excessive loads and incorrect loads on the ankles or even damages to the knee, hip and spine. In addition, the actuator-based signal transmitter(s) may also be used simultaneously together with other signal transmitters (e.g. acoustic or optical signal transmitters).

However, the afore-mentioned embodiment may also be used extensively in the field of training to train different loads on the foot in certain sports, such as bale running or running on the lateral edge of the foot.

According to a further embodiment of the present invention, the device further comprises (at least) one acoustic signal transmitter which serves as an additional feedback output unit and which receives the feedback control signal of the feedback control signal generator and outputs an acoustic feedback. In particular, the acoustic signal transmitter may be a loudspeaker attached to the outside area of the sole, which outputs signals according to the feedback control signal, e.g. digital tones. However, the acoustic signal transmitter must be mounted so as to be audible so that the user can hear the acoustic signals. In particular, the acoustic signal transmitter may also be used simultaneously together with other signal transmitters.

In an embodiment of the present invention, the device comprises at least one light emitting element as an additional feedback output unit which receives the feedback control signal of the feedback control signal generator and outputs a light signal. The light emitting element must be suitably positioned outside the shoe so that the user can see the light signals. In particular, the optical signal transmitter may also be used simultaneously together with other signal transmitters.

In a preferred embodiment of the present invention, the device further comprises a transmission unit for directly transmitting data and/or signals of the analyzing unit or the feedback control signal(s) of the feedback control signal generator to an external display unit. The transmission unit may be embodied as a wireless sensor or as a cable, wherein the wireless sensor is preferably mounted on the outside of the shoe, e.g. on the shoe laces, on the outside of the shoe or on the leg joint. The transmission unit according to the present invention is an optional unit that enables the user to have additional control, e.g. on a display.

In a preferred embodiment of the present invention the device is disposed in a shoe or a shoe like medical frame, wherein both a permanent attachment of the shoe insole, e.g. by gluing, and a removable shoe insole is possible.

In a preferred embodiment of the present invention, the invention further comprises a method of operating a device, as set forth above, comprising at least the following steps: measuring loads and/or partial loads using the at least one force sensor and generating a measurement signal indicating the loads and/or partial loads on the foot; analyzing the measurement signal received by the analyzing unit and generating a feedback control signal on the basis of the analysis by the analyzing unit and controlling a feedback output unit on the basis of the feedback control signal; and outputting a feedback signal via the feedback output unit on the basis of the feedback control signal.

In a further preferred embodiment of the present invention, the method comprises transmitting the feedback control signal to at least one feedback-output unit, which is an actuator, an optical or acoustic signal generator, for generating correspondingly a tactile feedback, an optical feedback or an acoustic feedback in order to enable a monitoring of loads and/or partial loads on the foot in the region of the shoe insole. As mentioned above, the tactile feedback is output in the region of the shoe insole.

It should be noted here that the described embodiments may also be combined with each other without delimiting the scope of protection of the present invention.

BRIEF DESCRIPTION OF DRAWINGS

The drawings of the preferred embodiments are briefly described hereinafter.

DETAILED DESCRIPTION OF DRAWINGS

Figure 1:
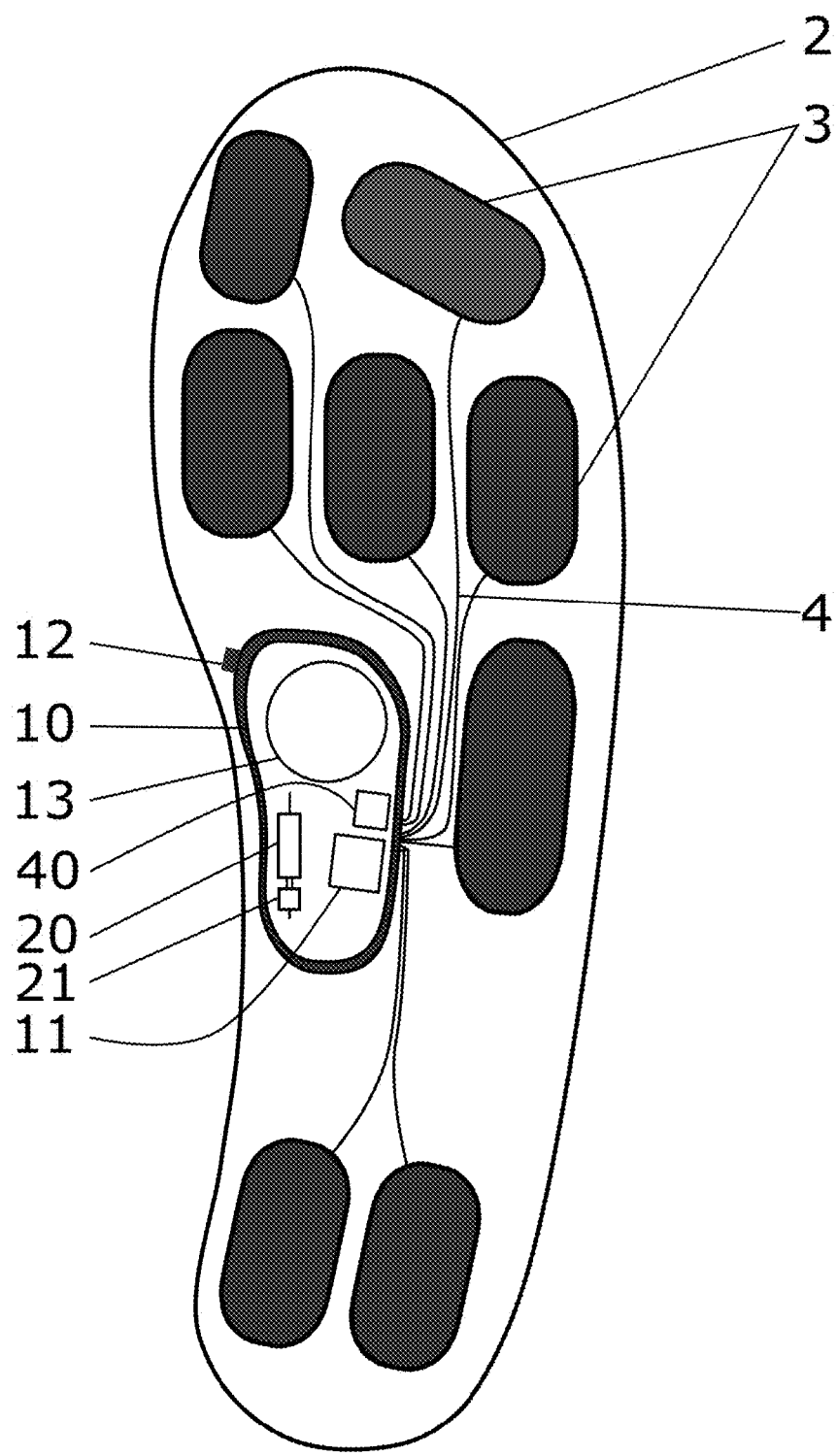
FIG. 1 shows a schematic view of a shoe insole, comprising the device according to a preferred embodiment of the present invention.

FIG. 1 shows a device 1 according to a preferred embodiment for avoiding excessive loads on a human foot when walking. The device 1 comprises a shoe insole (foot orthosis) 2 having at least one force sensor 3 for generating a measurement signal which indicates the loads and/or partial loads on the foot; an analyzing unit 11 which is connected to the at least one force sensor 3 via electrical cables 4 for analyzing the measurement signal from the at least one force sensor 3; an electric power source 13 for providing electric power to the analyzing unit 11; and a feedback control signal generator 20 which generates a feedback control signal on the basis of the analysis by the analyzing unit 11 to enable monitoring of loads and/or partial loads on the foot. Furthermore, the device 1 comprises an actuator 22 as a feedback output unit 21, which receives the feedback control signal and generates a tactile feedback in the region of the shoe insole 2. In the present embodiment, the sensitive components, i.e. the analyzing unit 11, the electric power source 13, the feedback control signal generator 20 and the actuator 22 are disposed in a sealed housing 10 to protect them from water and/or pressure loads. However, it is not absolutely necessary to seal the housing 10, e.g. for use in dry rooms, for example in physiotherapy.

According to FIG. 1, several force sensors 3 are distributed in the shoe insole and arranged in anatomically distinct regions. The figure shows a first group of force sensors 3 in the region of the toes of the human foot, especially in the respective contact region of the front ends of the toes with the shoe insole 2. Here, the large toe has a particular importance, which is reflected in a measuring region of a single force sensor 3, which is specially designed for this purpose. Conveniently, the other measuring regions of the force sensors 3 for the small toes are combined to form a separate force sensor. Alternatively, each of the small toes can be assigned its own force sensors 3 in the aforementioned manner. Furthermore, at least one force sensor 3 is arranged adjacent to the foot arch (not shown) in the region of the ball of the foot. In the example illustrated here, three force sensors 3 are arranged in the region of the ball of the foot, of which one force sensor 3 is preferably located at a central position on the shoe insole 2 and two additional force sensors 3 are arranged to the left and right of this central force sensor 3. Due to the two eccentric force sensors 3, it is generally possible to detect an incorrect lateral load on the foot, e.g. due to tilting or due to a tilted contact of the foot.

Furthermore, according to FIG. 1, an additional force sensor 3 is arranged to the side of the housing 10. Preferably, the housing 10 is arranged in the region of the longitudinal arch of the foot, so that this individual force sensor 3 is arranged directly next to the longitudinal arch of the foot, namely in that region in which the foot is usually supported by the foot orthosis 2. By means of this sensor, it is also possible to analyze force signals to determine how high the load is in the middle area of the foot and, in particular, whether it is an incorrect load due to lateral or tilted contact of the foot on one side when walking.

Furthermore, according to FIG. 1 at least one force sensor 3 is arranged in the region of the heel of the foot. Two force sensors 3 are preferably arranged in the region of the heel of the foot, either symmetrically or almost symmetrically to an imaginary longitudinal centerline of the insole. Due to these two eccentric force sensors 3 in the region of the heel, one may additionally detect an incorrect load on the foot, e.g. by an excessive contact of the foot in the region of the heel, e.g. in the case of so-called 'heel walkers'.

Preferably, the signals of the respective sensors (i.e. of the force sensors 3) are transmitted individually via the respective conductive tracks 4 to the analyzing unit 4, which may also read and process these signals individually. According to the present invention, a spatially resolved measurement of loads and/or partial loads on a human foot is possible in order to output a feedback signal on the basis of an appropriate analysis of the measurement signals, as will be described hereinafter.

If the device 1 for outputting the feedback signal comprises only one actuator 22, the multiple force measurement signals may be averaged to generate a feedback control signal. This averaging may generally be carried out over the entire area of the shoe insole 2. Optionally, the analyzing unit 11 may also be controlled or switched to an appropriate operating mode, so that not all force sensors 3, but only a subgroup of force sensors 3 is used for analyzing and for generating the feedback control signal. Conveniently, these groups correspond to the groups shown in FIG. 1. Two or more groups may also be logically interconnected to form a subgroup.

If the device 1 for outputting the feedback signal comprises a plurality of actuators 22, the above-mentioned averaging may also be used to generate a uniform feedback control signal for all actuators.

According to another embodiment, a plurality of actuators 22 may be arranged in the foot orthosis 2. For example, an actuator 22 may be arranged in the region of the longitudinal arch of the foot, e.g. in the manner as shown in FIG. 1, and another actuator 22 may be arranged in the region of the heel and/or another actuator 22 may be arranged in the region of the toe. In the latter case, groups of force sensors 3 may be assigned to the respective actuator 22, which are analyzed all together by the analyzing unit 11. In this way, a feedback signal may be provided at several regions of the shoe insole 2, preferably at two or three areas thereof.

In this embodiment of the present invention, device 1 is provided with an I/O interface 12 so that the device 1 can be read out and programmed, wherein the I/O interface 12 may be provided in particular as an NFC-interface and or as a plug-in interface, wherein at least one output thereof is disposed on the outer edge of the sealed housing 10. By reading out, for example, motion profiles may be read out and processed externally, which is particularly advantageous if several force sensors 3 are arranged in the shoe insole 2 in a distributed manner. By programming, for example, the assignment and/or logical interconnection of the force sensors 3 may be changed for analyzing the force signals. As a result, according to the present invention the device can be quickly reprogrammed to other users.

Figure 2:
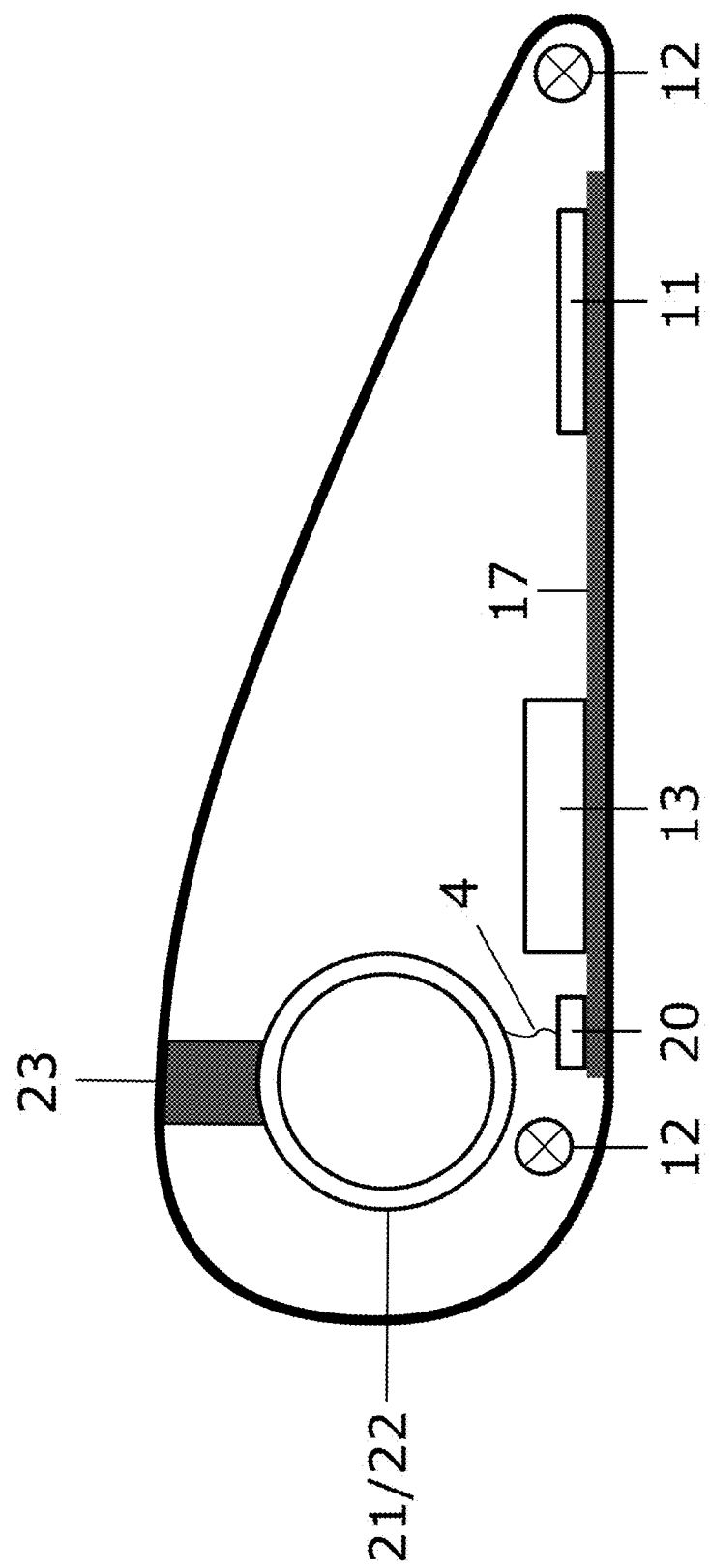
FIG. 2 shows a schematic sectional view through the sealed housing of the device according to a preferred embodiment of the present invention.

FIG. 2 shows a schematic detailed view of the sealed housing 10 of the device 1 according to the previous embodiment of the present invention.

Conveniently, the housing 10 is a plastic housing of a suitable shape having a cavity in which the electronic components mentioned below are accommodated. The housing may be designed as a disposable housing in which these electronic components are encapsulated or embedded. According to other embodiments, the housing 10 may also be opened, for example by loosening a clip or screw connection. Furthermore, the housing also has suitable cable lead throughs for the conductive tracks 4, so that the electrical signals can be fed into and out of the housing. Conveniently, the conductive tracks 4 may be cast directly into the housing 10, whereby a sealing is achieved automatically. Specially designed cable lead throughs are also conceivable, however.

According to FIG. 1, the housing 10 is disposed in the region of the longitudinal arch of the foot, i.e. in the region of a raised region of the foot in which generally no major loads are applied. Nevertheless, the housing 10 should have a suitable minimum stability to provide adequate support for the foot in this region, while at the same time providing adequate protection for the electronic components.

As can be seen from the sectional view according to FIG. 2, conveniently the housing 10 is designed to correspond to an average shape of a longitudinal arch of the foot. This causes the gently curved shape shown in FIG. 2 to be formed lengthwise at the rear end of housing 10 and a much stronger curvature at the front end of housing 10. In the transverse direction, the housing 10 is generally wedge-shaped toward the outer edge of shoe insole 2. Due to the shape of the housing 10, the longitudinal arch of the foot can also be supported, for example in the form of an orthopaedic shoe insole (foot orthosis).

Generally, an additional force sensor 3 may also be provided on the upper side of the housing 10, or along its edge, which specifically can detect incorrect loads in the region of the longitudinal arch of the foot.

According to FIG. 2, the sealed housing 10 accommodates an electrical circuit board 17 on which the analyzing unit 11, the electric power source 13 and the feedback control signal generator 20 as well as other electronic components are disposed. In particular, the feedback output unit 21 may also be disposed on the printed circuit board. Although depicted in FIG. 2 as separate electronic components, all functions may be integrated into a suitable processor unit, in particular an MCU (microcontroller unit).

The feedback control signal is output to the actuator 22, which acts as a feedback output unit to generate a feedback signal in the event of an incorrect load or excessive load on the foot. In the case of a normal load, i.e. when the analyzing unit 11 determines on the basis of predetermined criteria that there are no incorrect loads or excessive loads, the feedback output unit should not generate a feedback signal. This is preferably output only if incorrect loads or excessive loads on the foot have been determined by the analyzing unit 11.

Such a criterion could be a threshold value for the force signal of a particular force sensor 3 or for the above-mentioned averaged force signal. If several force sensors 3 are provided, several threshold values may be specified, which may also be different from each other. These threshold values may be fixed, but may also be varied by the above-mentioned programming via the I/O interface 12. For example, motion profiles can be read out via the I/O interface 12 and analyzed externally, for example on the computer of a physiotherapist. He or she can determine suitable threshold values for the respective patient using suitable software.

The actuator 22 is preferably located on the upper side of the housing 10, which is of particular advantage if the actuator 22 is to transmit vibrations or displacement movements directly to the upper side of the shoe insole 2 and thus to the longitudinal arch of a person's foot, because in this way a tactile feedback signal can be transmitted directly to the person. It has been shown that the underside of the longitudinal arch of the foot is a very sensitive area, so that even a low signal strength can be perceived by the person. This ensures a low energy consumption.

Of course, the actuator 22 may also be provided at any other area of the shoe insole 2, in particular on the upper side or directly underneath a fabric cover of the shoe insole 2. Additional positions may basically be: the region to the side next to the longitudinal arch of the foot, i.e. where the foot is supported by a relatively high force of weight on the foot orthosis; the region of the heel of the foot orthosis, for example sideways or between the two force sensors 3 in the region of the heel (cf. FIG. 1); the region of the bale of the shoe insole 1, for example sideways or between the force sensors 3 in the region of the bale (cf. FIG. 1). It is preferred if the respective actuator does not overlap with a force sensor 3 to ensure a high measuring accuracy.

In principle, also a plurality of actuators may be arranged in shoe insole 2, particularly at the above-mentioned positions.

As shown in FIG. 2, the actuator 22 may also be mechanically coupled with a transmission element 23 in order to selectively transfer tactile stimuli to a desired region on the upper side of the shoe insole 2. For example, the transmission element 23 may not extend beyond the upper surface of the housing 10 in an idle state, i.e. in an inactive state, but may extend beyond the upper surface of the housing 10 in an activated state, i.e. in a state with tactile enervation of the underside of the foot, i.e. it can move back and forth for tactile stimulus transmission to the underside of the foot.

However, for a tactile transmission of stimuli it generally may also be sufficient if a vibration of the housing 10 or of the upper side thereof facing the shoe insole 2 is generated. For this purpose, an upper and lower part of the housing may be mounted in a manner to be displaceable relative to each other.

As a possible position of the actuator 22, a position directly below the upper part of the housing may also be selected, so that the tactile stimulus is transmitted directly to the housing 10, in particular directly to its upper part.

Figure 3:
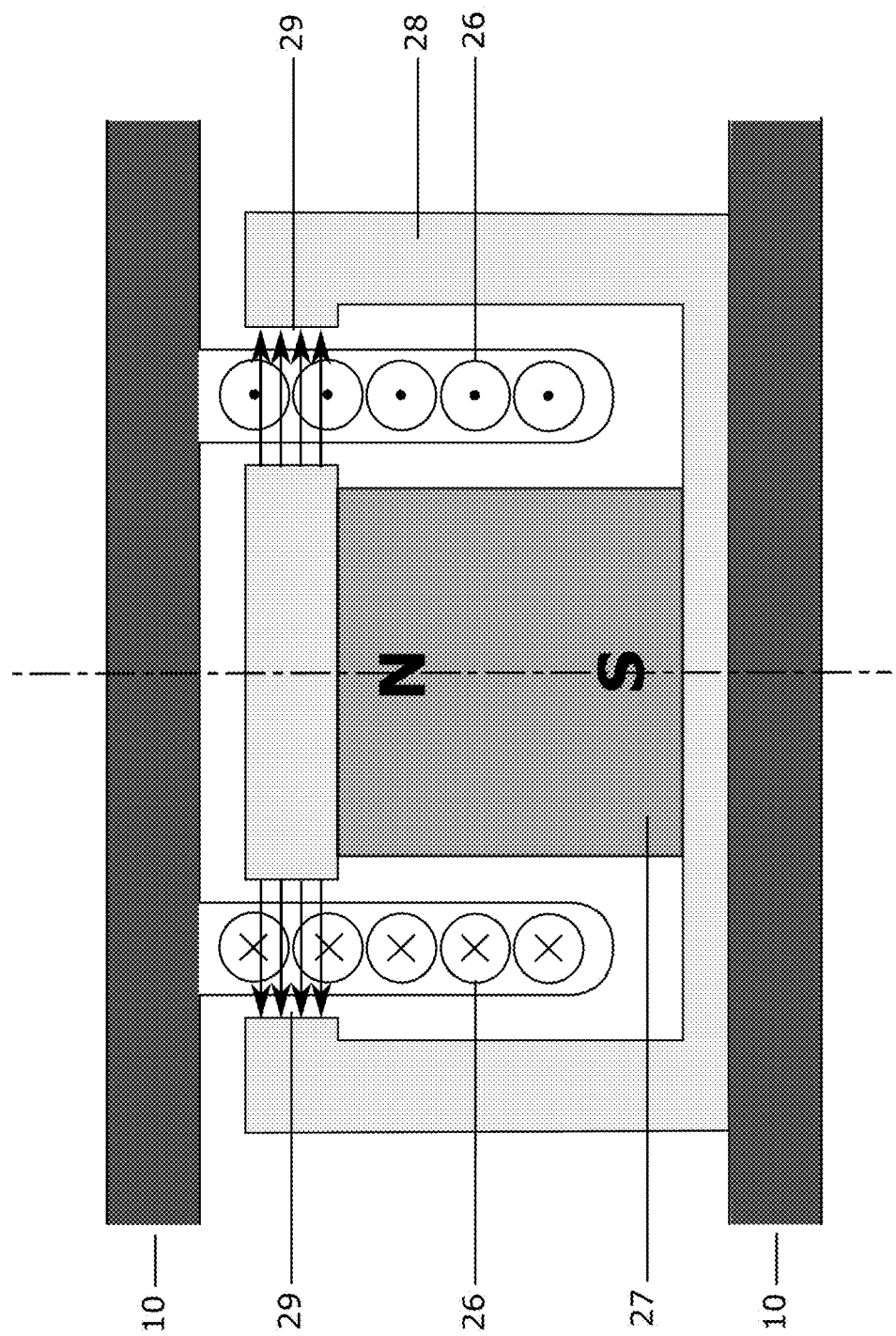
FIG. 3 shows a schematic sectional view of a tactile actuator of the device according to a particularly preferred embodiment of the present invention.

FIG. 3 shows an embodiment of the actuator 22, which represents a feedback output unit according to another embodiment of the present invention. This actuator 22 comprises a permanent magnet 27, which is arranged in the centre of the actuator, as well as a soft magnetic guiding material 28, which is arranged in the outer region of the actuator 22 and two exciting coil structures 26, which are arranged symmetrically to a centerline of the actuator 22 and which are fixed to an upper side of the sealed housing 10 and which are immersed in corresponding openings of the actuator. The actuator 22 is thus configured similar to a loudspeaker, wherein the permanent magnet 27 together with the soft magnetic guiding material 28 is connected to the lower part of the sealed housing 10 for guiding the magnetic flux. When a varying current flows through the excitation coil 26, excitation coil 26 and permanent magnet 27 exert a force along the magnetic field lines 29, which is transmitted to the longitudinal arch of the foot via the upper side of the housing 10. Thus, a bio-feedback signal is transmitted to the foot.

Basically, it is possible to use the same principle in reverse also as a force sensor 3, wherein with this functionality the movement of the foot presses the coils downwards, whereby a current is induced in the coils, which can be used as a measurement signal. This configuration allows the element from FIG. 3 to be used as an actuator or as a force sensor 3.

Figure 4B:
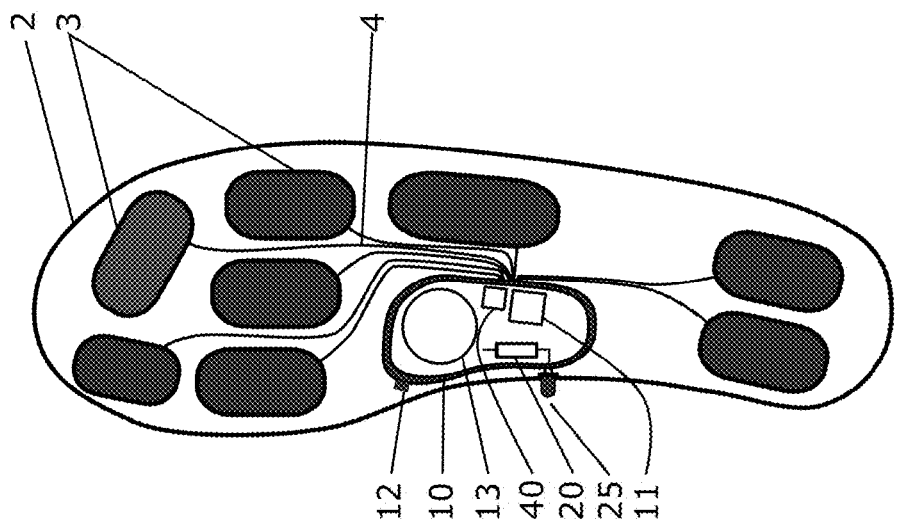
FIG. 4b shows a schematic view of a shoe insole, comprising the device according to an embodiment of the present invention with an additional light emitting element.
Figure 4A:
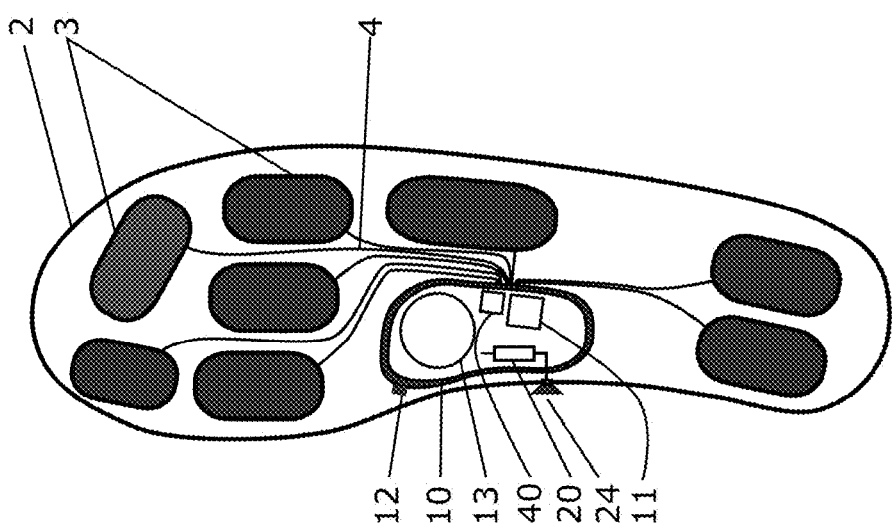
FIG. 4a shows a schematic view of a shoe insole, comprising the device according to another preferred embodiment of the present invention, in which an additional acoustic signalling device is provided.

FIGS. 4a and 4b show further embodiments according to the present invention. FIG. 4a shows an embodiment in which the feedback control signal generator 20 is connected to an acoustic signal generator 24 as feedback output unit 21, which receives the feedback control signal and outputs an acoustic signal for monitoring loads and/or partial loads on the foot. The acoustic signal transmitter 24 preferably may be embodied as a simple loudspeaker and may be attached, for example, to the edge of the shoe insole 2 or preferably outside the shoe, so that the acoustic signal can be heard by the user. FIG. 4b shows a further embodiment, in which the feedback control signal generator 20 is connected to an optical signal generator or light emitting element 25 as a feedback output unit 21, which receives the feedback control signal and outputs a light signal for monitoring loads and/or partial loads on the foot. The light emitting element 25 may be embodied particularly as an LED and is preferably located in the front outer area of the shoe. For this purpose, a suitable cable connection between the shoe insole 2 and the outside of the shoe is required, on which the optical signal transmitter or light emitting element 25 is arranged.

Figure 5:
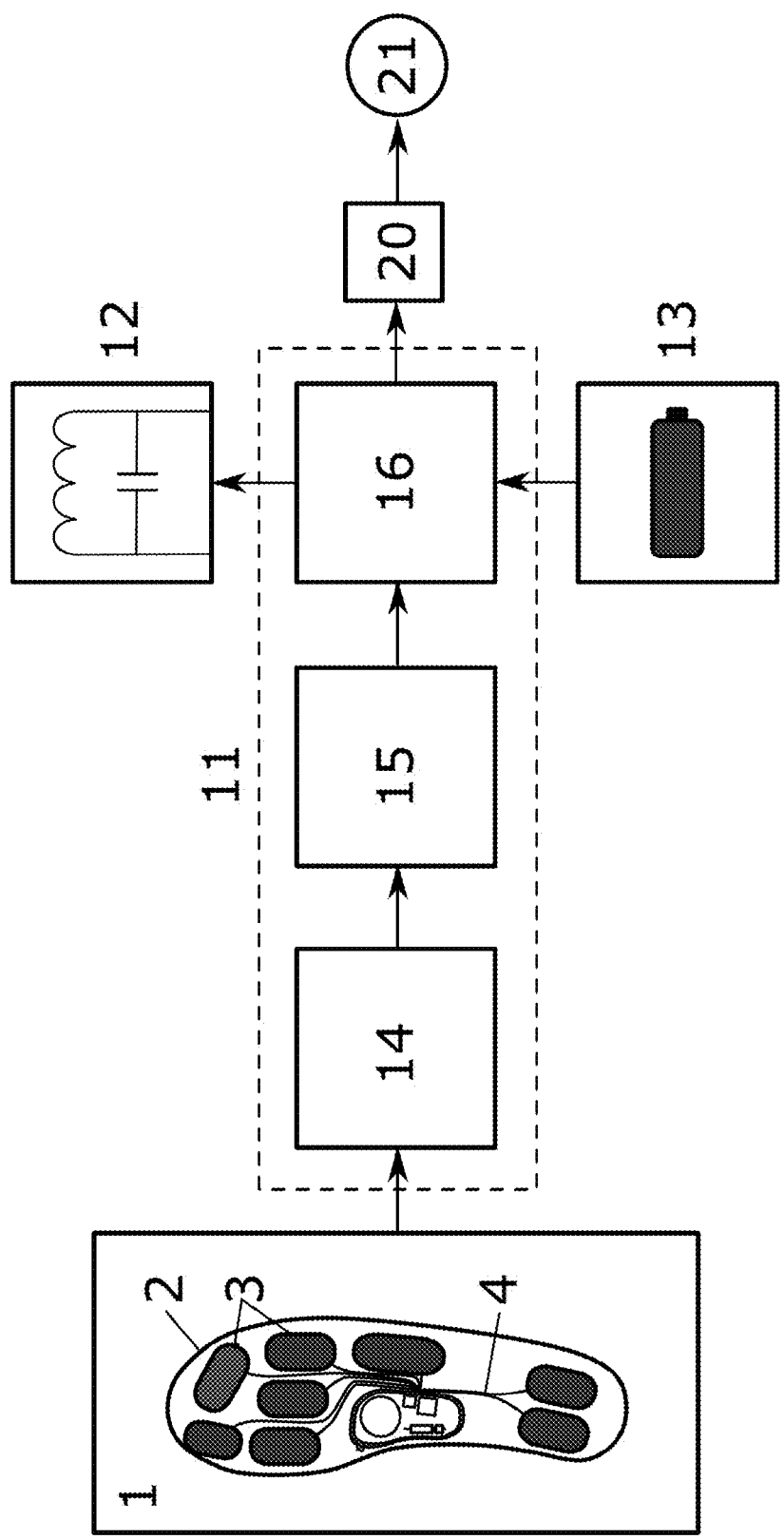
FIG. 5 shows a block diagram of a particularly preferred embodiment of the present invention.

FIG. 5 shows a block diagram of an embodiment of the present invention. In this case, sensors 3 of device 1 first measure the forces generated by the foot and then transmit a plurality of analog measurement signals to the respective inputs of a multiplexer 14, which then forward the respective signals to an analog/digital converter 15, which converts them into digital signals and forwards them to a microcontroller (MCU) 16, which processes them further. The aforementioned units 14, 15 and 16 form at least a part of the analyzing unit 11. The MCU 16 may also interact with signals from the I/O interface 12. The entire electronic system is powered by the electric power source 13. After appropriate analysis of the measurement signals, as described above, the feedback control signal generator 20 is driven to generate a feedback control signal which is transmitted to the feedback signal output unit 21, which then outputs a feedback signal, in particular a tactile feedback as described above.

Due to the above-mentioned configuration, film sensors already available on the market may be used as force sensors in the device 1, wherein the force sensors conveniently are scanned periodically for reading out the measurement signals and then processing them further, as described above. A linearization of the characteristic curves of the sensors may be required to read out the measurement signals. In principle, however, such a linearization may also be carried out in the MCU 20 on the basis of the read out measurement signals. Furthermore, for analyzing the measurement signals, an average load value may be calculated by summing up, e.g. over all force sensors 3 of the shoe insole 2 or also over subgroups thereof, as described above. If a predetermined threshold value is exceeded, the actuator may be controlled to generate a feedback signal. The threshold values may be set in the MCU via I/O interface 12 and are usually stored as parameters in the MCU.

Figure 6:
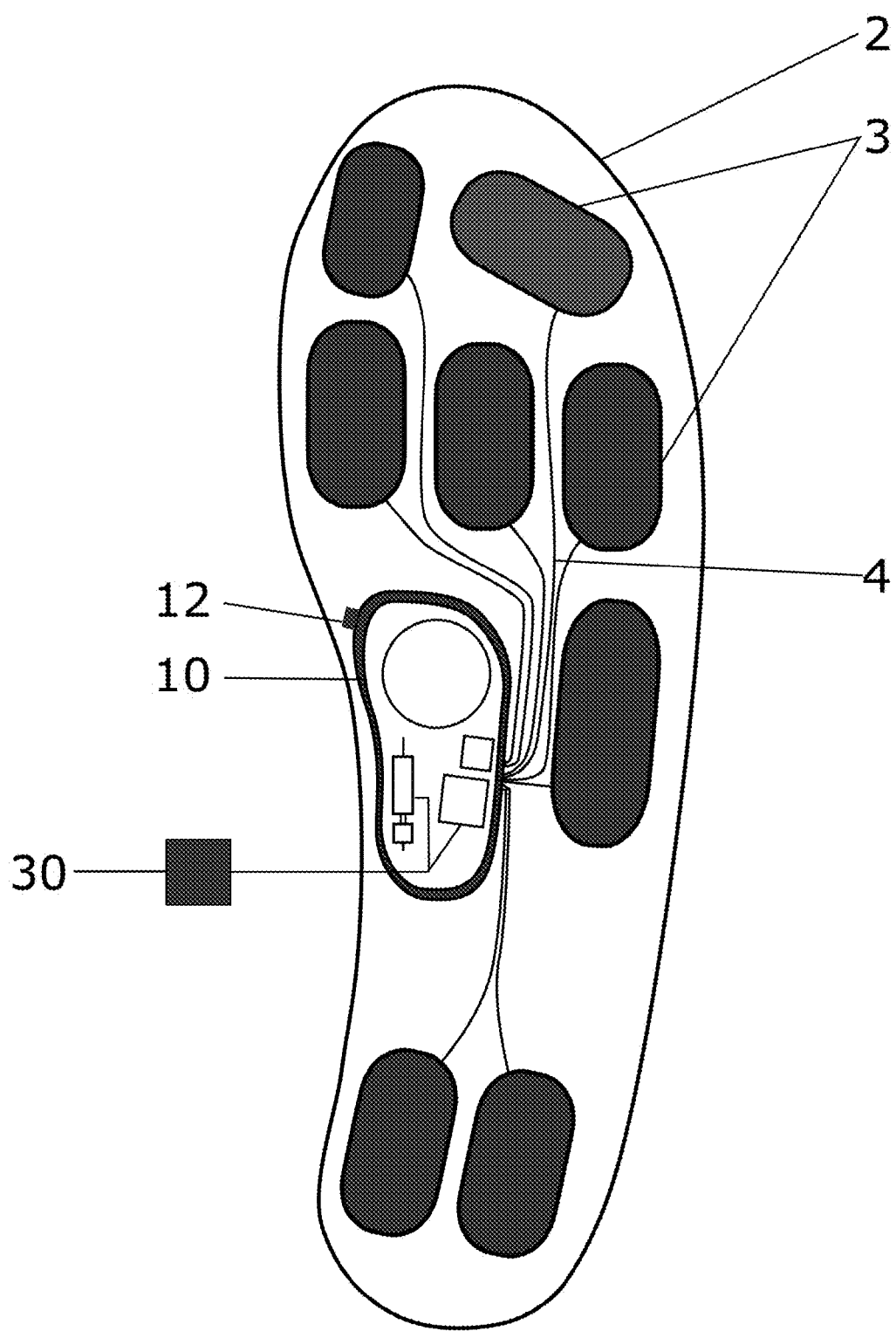
FIG. 6 shows a schematic view of a shoe insole, comprising the device according to another preferred embodiment of the present invention in which an additional transmission unit is also provided.

FIG. 6 shows another possible embodiment of the device 1 according to the present invention, in which a transmission unit 30 is arranged in addition to the tactile feedback output, by means of which the device 1 can exchange data with an external display unit, such as a smartphone or a display unit. In particular, the current state of the loads on the foot can be displayed. The transmission unit 30 may be embodied in particular as a cable or preferably as an RF transmitter, but the RF transmitter must be located outside the shoe to ensure signal transmission. If the RF transmitter is mistakenly attached directly to or underneath the shoe insole, the foot may shield the RF transmitter and interfere with or even completely prevent reliable reception.

LIST OF REFERENCE NUMERALS

1 device for avoiding excessive loads on the human foot when walking
2 shoe insole
3 force sensor(s)
4 electric cables
10 sealed housing
11 analyzing unit or CPU
12 I/O interface (plug-in connection or NFC induction coil)
13 electric power source
14 multiplexer
15 analog-to-digital converter
16 microcontroller (MCU)
17 electrical circuit board
20 feedback control signal generator (output stage)
21 feedback output unit
22 actuator
23 transmission member
24 acoustic signal transmitter
25 optical signal transmitter or light emitting element
26 excitation coil
27 permanent magnet
28 soft magnetic guiding material
29 magnetic field lines
30 transmission unit
31 external wireless sensor
32 cables
40 memory element

The invention claimed is:
1. A device for avoiding excessive loads on the human foot when walking, comprising:
 a shoe insole having at least one force sensor for generating a measurement signal which indicates loads and/or partial loads on the foot when walking;
 an analyzing unit electrically connected to the at least one force sensor for analyzing the measurement signal of the at least one force sensor;
 an electric power source for providing electric power to the analyzing unit; and
 a feedback control signal generator and at least one feedback output unit; wherein
 the feedback control signal generator generates a feedback control signal on the basis of the analysis by the analyzing unit, and
 the at least one feedback output unit is controlled by the feedback control signal to output a feedback signal due to loads and/or partial loads on the foot, wherein
 the analyzing unit, the energy source and the feedback control signal generator are disposed as a common unit in a housing which is integrated into the shoe insole in the region of its foot longitudinal arch, the housing being designed in such a way as to directly support a foot in the region of the foot longitudinal arch, wherein
 the at least one feedback output unit is an actuator, which receives the feedback control signal, is disposed on the housing or directly at the housing and outputs a tactile feedback in the region of the foot longitudinal arch, wherein
 the actuator is configured for generating, as the tactile feedback, vibrations on the housing or in the immediate vicinity of the housing, said actuator comprising:
 a permanent magnet disposed at a central position,
 a soft magnetic guiding material disposed in the outer region of the actuator, and
 an excitation coil arranged symmetrically around the centerline of the actuator and connected to a plate arranged on the upper side of the shoe insole or in its immediate vicinity, wherein
 the excitation coil is immersed in a corresponding opening of the actuator to be substantially perpendicular to the magnetic field lines of the permanent magnet, and
 a tactile feedback is generated by generating a current flow in the excitation coil.

2. The device for avoiding excessive loads on the human foot when walking as claimed by claim 1, comprising a plurality of force sensors distributed in or on the shoe insole.

3. The device for avoiding excessive loads on the human foot when walking as claimed by claim 1, wherein the analyzing unit sums up measurement signals of a plurality of force sensors and generates the feedback control signal on the basis of a mean value or sum value.

4. The device for avoiding excessive loads on the human foot when walking as claimed by claim 1, said device comprising a plurality of force sensors and a plurality of actuators distributed in or on the shoe insole and providing tactile feedback at a plurality of positions of the shoe insole.

5. The device for avoiding excessive loads on the human foot when walking as claimed by claim 1, wherein the housing comprises an electrical circuit board and the analyzing unit, the electric power source and the feedback control signal generator are disposed in the housing.

6. The device for avoiding excessive loads on the human foot when walking as claimed by claim 1, further comprising at least one I/O interface for reading out and/or programming the device.

7. The device for avoiding excessive loads on the human foot when walking as claimed by claim 1, further comprising a memory element for storing data of the analyzing unit.

8. The device for avoiding excessive loads on the human foot when walking as claimed by claim 1, further comprising a transmission unit for transmitting data and/or signals of the analyzing unit or the feedback control signal of the feedback control signal generator to an external display unit.

9. The device for avoiding excessive loads on the human foot when walking as claimed by claim 8, wherein the transmission unit is an RF sensor provided externally to the shoe insole.

10. A shoe having a device for avoiding excessive loads on the human foot when walking, comprising
a shoe insole having at least one force sensor for generating a measurement signal indicating loads and/or partial loads on the foot when walking;
an analyzing unit electrically connected to the at least one force sensor for analyzing the measurement signal of the at least one force sensor;
an electric power source for providing electric power to the analyzing unit; and
a feedback control signal generator and at least one feedback output unit (21); wherein
the feedback control signal generator generates a feedback control signal on the basis of the analysis by the analyzing unit, and
the at least one feedback output unit is controlled by the feedback control signal to output a feedback signal due to loads and/or partial loads on the foot, wherein
the analyzing unit, the energy source and the feedback control signal generator are disposed as a common unit in a housing which is integrated into the shoe insole in the region of its foot longitudinal arch, the housing being designed in such a way as to directly support a foot in the region of the foot longitudinal arch, wherein
the at least one feedback output unit is an actuator, which receives the feedback control signal, is disposed on the housing or directly at the housing and outputs a tactile feedback in the region of the foot longitudinal arch; wherein
the actuator is configured for generating, as the tactile feedback, vibrations on the housing or in the immediate vicinity of the housing, and wherein the actuator comprises:
a permanent magnet disposed at a central position,
a soft magnetic guiding material disposed in the outer region of the actuator, and
an excitation coil arranged symmetrically around the centerline of the actuator and connected to a plate arranged on the upper side of the shoe insole or in its immediate vicinity, wherein
the excitation coil is immersed in a corresponding opening of the actuator to be substantially perpendicular to the magnetic field lines of the permanent magnet, and
a tactile feedback is generated by generating a current flow in the excitation coil.

11. A method of operating a device for avoiding excessive loads on the human foot when walking, said device for avoiding excessive loads on the human foot when walking comprising:
a shoe insole having at least one force sensor for generating a measurement signal which indicates loads and/or partial loads on the foot when walking;
an analyzing unit electrically connected to the at least one force sensor for analyzing the measurement signal of the at least one force sensor;
an electric power source for providing electric power to the analyzing unit; and
a feedback control signal generator and at least one feedback output unit; wherein
the feedback control signal generator generates a feedback control signal on the basis of the analysis by the analyzing unit, and
the at least one feedback output unit is controlled by the feedback control signal to output a feedback signal due to loads and/or partial loads on the foot
said method comprising the steps:
measuring loads and/or partial loads using the at least one force sensor (3) and generating a measurement signal indicating the loads and/or partial loads on the foot;
analyzing the measurement signal received by the analyzing unit and generating a feedback control signal on the basis of the analysis by the analyzing unit and controlling the at least one feedback output unit to output a feedback signal due to loads and/or partial loads on the foot; and
outputting the feedback signal via the at least one feedback output unit; wherein
the housing directly supports the foot in the region of the foot longitudinal arch, and
the actuator receives the feedback control signal and outputs a tactile feedback in the region of the foot longitudinal arch and on the housing or in the immediate vicinity of the housing; wherein
vibrations are generated as tactile feedback on the housing or in the immediate vicinity of the housing using an actuator that comprises:
a permanent magnet disposed at a central position,
a soft magnetic guiding material disposed in the outer region of the actuator, and
an excitation coil arranged symmetrically around the centerline of the actuator and connected to a plate arranged on the upper side of the shoe insole or in its immediate vicinity, wherein
the excitation coil is immersed in a corresponding opening of the actuator to be substantially perpendicular to the magnetic field lines of the permanent magnet, and
a tactile feedback is generated by generating a current flow in the excitation coil.

12. A device for avoiding excessive loads on the human foot when walking, comprising:
a shoe insole having at least one force sensor for generating a measurement signal which indicates loads and/or partial loads on the foot when walking;

an analyzing unit electrically connected to the at least one force sensor for analyzing the measurement signal of the at least one force sensor;
an electric power source for providing electric power to the analyzing unit; and
a feedback control signal generator and at least one feedback output unit; wherein
the feedback control signal generator generates a feedback control signal on the basis of the analysis by the analyzing unit, and
the at least one feedback output unit is controlled by the feedback control signal to output a feedback signal due to loads and/or partial loads on the foot, wherein
the analyzing unit, the energy source and the feedback control signal generator are disposed as a common unit in a housing which is integrated into the shoe insole in the region of its foot longitudinal arch, the housing being designed in such a way as to directly support a foot in the region of the foot longitudinal arch, wherein
the at least one feedback output unit is an actuator, which receives the feedback control signal, is disposed on the housing or directly at the housing and outputs a tactile feedback in the region of the foot longitudinal arch, and wherein
the feedback control signal generator generates the feedback control signal on the basis of the analysis by the analyzing unit such that
when the measurement signal of the at least one force sensor is within an acceptable range, the actuator does not out a tactile feedback, and
when the measurement signal of the at least one force sensor is no longer within the acceptable range, the actuator outputs a tactile feedback.

13. A device for avoiding excessive loads on the human foot when walking, comprising:

a shoe insole having at least one force sensor for generating a measurement signal which indicates loads and/or partial loads on the foot when walking;
an analyzing unit electrically connected to the at least one force sensor for analyzing the measurement signal of the at least one force sensor;
an electric power source for providing electric power to the analyzing unit; and
a feedback control signal generator and at least one feedback output unit; wherein
the feedback control signal generator generates a feedback control signal on the basis of the analysis by the analyzing unit, and
the at least one feedback output unit is controlled by the feedback control signal to output a feedback signal due to loads and/or partial loads on the foot, wherein
the analyzing unit, the energy source and the feedback control signal generator are disposed as a common unit in a housing which is integrated into the shoe insole in the region of its foot longitudinal arch, the housing being designed in such a way as to directly support a foot in the region of the foot longitudinal arch, wherein
the at least one feedback output unit is an actuator, which receives the feedback control signal, is disposed on the housing or directly at the housing and outputs a tactile feedback in the region of the foot longitudinal arch, wherein
the actuator is configured as a rotating micro motor with eccentric members, as a vibrator with exclusively translational direction of movement or as a unit having an excitation coil firmly connected to an upper part of the housing and a permanent magnet connected to a lower part of the housing together with a soft magnetic guiding material for guiding magnetic flow, for generating, as the tactile feedback, vibrations on the housing or in the immediate vicinity of the housing.

* * * * *